United States Patent [19]
Bucher

[11] Patent Number: 6,053,893
[45] Date of Patent: Apr. 25, 2000

[54] DEVICE FOR THE DOSED RELEASE OF AN INJECTABLE PRODUCT

[75] Inventor: Eugen Bucher, Mühlethurnen, Switzerland

[73] Assignee: Disetronic Licensing AG, Switzerland

[21] Appl. No.: 09/132,268

[22] Filed: Aug. 11, 1998

[51] Int. Cl.$^7$ ..................................................... A61M 5/20
[52] U.S. Cl. ..................... 604/131; 604/135; 128/DIG. 1
[58] Field of Search ................................... 604/131, 134, 604/135, 207, 208; 128/DIG. 1

[56] References Cited

U.S. PATENT DOCUMENTS

| | | |
|---|---|---|
| 4,592,745 | 6/1986 | Rex et al. . |
| 4,865,591 | 9/1989 | Sams . |
| 4,883,472 | 11/1989 | Michel . |
| 4,946,446 | 8/1990 | Vadher . |
| 4,973,318 | 11/1990 | Holm et al. . |
| 5,017,190 | 5/1991 | Simon et al. . |
| 5,084,060 | 1/1992 | Freund et al. . |
| 5,114,406 | 5/1992 | Gabriel et al. . |
| 5,273,544 | 12/1993 | Van der Wal ............................ 604/134 |
| 5,279,579 | 1/1994 | D'Amico . |
| 5,279,585 | 1/1994 | Balkwill . |
| 5,292,314 | 3/1994 | D'Alessio et al. . |
| 5,295,976 | 3/1994 | Harris . |
| 5,320,609 | 6/1994 | Haber et al. ............................. 604/135 |
| 5,336,183 | 8/1994 | Greelis et al. . |
| 5,338,311 | 8/1994 | Mahukar . |
| 5,370,629 | 12/1994 | Michel et al. . |
| 5,472,430 | 12/1995 | Vaillancourt et al. . |
| 5,496,293 | 3/1996 | Huggenberger . |
| 5,514,097 | 5/1996 | Knauer . |
| 5,527,294 | 6/1996 | Weatherford et al. . |
| 5,549,558 | 8/1996 | Martin . |
| 5,549,575 | 8/1996 | Giambattista et al. . |
| 5,573,510 | 11/1996 | Isaacson . |
| 5,582,598 | 12/1996 | Chanoch . |
| 5,591,136 | 1/1997 | Gabriel . |
| 5,591,138 | 1/1997 | Vaillancourt . |
| 5,593,390 | 1/1997 | Castellano et al. . |
| 5,609,577 | 3/1997 | Haber et al. . |
| 5,643,214 | 7/1997 | Marshal et al. . |
| 5,658,259 | 8/1997 | Pearson et al. . |
| 5,674,204 | 10/1997 | Chanoch . |
| 5,679,111 | 10/1997 | Hjertman et al. .................. 604/207 X |
| 5,725,508 | 3/1998 | Chanoch et al. . |
| 5,728,074 | 3/1998 | Castellano et al. . |
| 5,743,889 | 4/1998 | Sams . |
| 5,779,677 | 7/1998 | Frezza ..................................... 604/134 |

FOREIGN PATENT DOCUMENTS

| | | |
|---|---|---|
| 3638984 | 11/1986 | Denmark . |
| 3645245 | 11/1986 | Denmark . |
| 3900926 | 8/1989 | Denmark . |
| 0037696 | 3/1981 | European Pat. Off. . |
| 0058536 | 8/1982 | European Pat. Off. . |
| 0245312 | 10/1986 | European Pat. Off. . |
| 0268191 | 11/1987 | European Pat. Off. . |
| 0298067 | 6/1988 | European Pat. Off. . |
| 327910 | 1/1989 | European Pat. Off. . |
| 0373321 | 6/1990 | European Pat. Off. . |

(List continued on next page.)

*Primary Examiner*—John D. Yasko
*Attorney, Agent, or Firm*—Dorsey & Whitney LLP

[57] ABSTRACT

Device for the dosed release of an injectable product, comprising a housing, a retainer for a container, containing the product, in which a piston is displaceably accommodated, whose displacement in a feed direction causes the release of a product dose, a driven member including a driven rod which protruding into the container when the container is accommodated in the housing pushes the piston in the feed direction to release the product, at least one drive member engaging with the driven member, the driven member being displaced in the feed direction by the activation of the drive member, wherein the driven member contains a driven bush surrounding the driven rod, which driven bush engages into the drive member and is displaced together with the driven rod, and a rear wall—in relation to the feed direction—of the container protrudes at least during a release into an annulus formed between the driven rod and the driven bush.

9 Claims, 2 Drawing Sheets

FOREIGN PATENT DOCUMENTS

| | | |
|---|---|---|
| 496141 | 1/1991 | European Pat. Off. . |
| 0516473 | 5/1992 | European Pat. Off. . |
| 0498737 | 8/1992 | European Pat. Off. . |
| 0554995 | 8/1993 | European Pat. Off. . |
| 0594349 | 4/1994 | European Pat. Off. . |
| 0627229 | 5/1994 | European Pat. Off. . |
| 2701211 | 8/1994 | France . |
| 3840000 | 11/1988 | Germany . |
| 4013769 | 4/1990 | Germany . |
| 4223958 | 7/1992 | Germany . |
| 19519147 | 5/1995 | Germany . |
| 8702895 | 5/1987 | WIPO . |
| 9110460 | 7/1991 | WIPO . |
| 9305835 | 8/1992 | WIPO . |
| 9218179 | 10/1992 | WIPO . |
| 9316740 | 9/1993 | WIPO . |
| 9409841 | 5/1994 | WIPO . |
| 9415210 | 7/1994 | WIPO . |
| 9501812 | 1/1995 | WIPO . |
| 9504563 | 2/1995 | WIPO . |
| 9607443 | 3/1996 | WIPO . |

DEVICE FOR THE DOSED RELEASE OF AN INJECTABLE PRODUCT

BACKGROUND OF THE INVENTION

1. Field of the Invention

The invention refers to a device for the dosed release of an injectable product, wherein the driven member contains a driven bush surrounding the driven rod, which driven bush engages into the drive member and is displaced together with the driven rod, and a rear wall—in relation to the feed direction—of the container protrudes at least during a release into an annulus formed between the driven rod and the driven bush.

2. Description of the Related Art

Devices such as the invention are preferably devices for the injection or infusion of a liquid drug solution, preferably a liquid medication such as insulin or hormone preparation solutions. Particularly preferred are portable devices, especially in the form of so-called injection pens which hereinafter are also representative for other devices.

Known injection pens but also pump devices for the infusion or infusion/injection of drug solutions contain a housing in which a container containing the product can be accommodated in a specially provided retainer. Within this container, a piston is displaceably accommodated. When the piston is moved in a feed direction, a product dose is released as a result of the piston displacement. For this purpose, the container, generally an ampoule, is fixed in the retainer in such a way that a driven member of a drive means forces the piston to move in feed direction to release the product. The driven member contains a driven rod protruding into the container towards the piston if the container is contained in the housing. A drive member of the drive means makes contact with the driven member in such a way that by activating the drive member, the driven member can be displaced in feed direction. The drive means is preferably at least a single-stage spindle drive. In known injection pens with spindle drives, the drive member, preferably formed as a drive bush, is activated by rotation in order to dose the product dose to be released with the next injection and also by straight displacement in the feed direction of the piston, i.e. by manually exerted pressure. In known pump devices with spindle drives, the drive member is only activated by rotation. The rotation in turn causes a forward displacement of the driven member which in pump devices is generally directly transferred onto the piston.

In particular for a portable device which is carried by the user, the external dimensions of the device should be as small as possible. Of special significance is a reduction of the length of the means or device in the feed direction. As a result, either the entire means including the container containing the product can be made smaller or a longer container can be used if the overall length remains the same. The longer container may accommodate more product. The longer container could, however, also be a so-called double-chamber ampoule in which the product and a solution fluid are contained in two separate chambers arranged in series and are only mixed immediately before the first injection or infusion.

SUMMARY OF THE INVENTION

It is the task of the invention to reduce the length of such a generic means.

The task is solved by a device for the dosed release of an injectable product, comprising a housing, a retainer for a container containing the product, in which a piston is displaceably accommodated, whose displacement in a feed direction causes the release of a product dose, a driven member including a driven rod which protruding into the container when the container is accommodated in the housing pushes the piston in the feed direction to release the product, at least one drive member engaging with the driven member, the driven member being displaced in the feed direction by the activation of the drive member.

According to the invention, the driven member contains a driven rod and a driven bush surrounding the driven rod. The driven bush engages with a drive member in such a way that in case of an activation of the drive member, the driven rod and the driven bush are displaced. At the same time, a rear wall of the product container as seen in relation to the feed direction of the piston can, as a result of this design of the driven member, be accommodated at least during the release of the product in an annulus of the driven member formed between the driven rod and the driven bush. The driven bush preferably contains an engaging means on an external surface for engaging with the drive member; the engaging means is preferably an external thread.

When using a spindle drive as a drive means, the drive member, preferably formed as a drive bush and surrounding the driven member, can slide over the container. The drive and driven member are advantageously slid over the container like a shell. In injection devices and in particular in injection pens in which the forward displacement of the piston is caused by sliding the drive and driven member forwards, the drive member can be positioned particularly closely to the container. This reduces the length of the means or device.

The driven rod and the driven bush are preferably designed as a single component. Particularly preferred is a pot-shaped driven member with a bottom from which the driven rod and the driven bush rise up vertically. If the housing of the means is an enclosed housing such as the housing of an injection pen, the housing contains at least two hollow cylindrical walls with an annulus therebetween into which the drive member and the driven bush can be displaced during an injection or infusion.

Where the container containing the product is a double ampoule with two separate chambers arranged in series, such a housing contains three hollow cylindrical walls arranged shell-like to one another. Between the outer and the middle wall an annulus is formed, into which the drive means can be displaced whilst a second annulus is formed between the inner and the middle wall which opens on the side facing away from the drive means. The ampoule which is open at the rear is slid into this second annulus and fixed therein upon insertion into the housing. The innermost of the three said walls serves as a mixing tube during this operation. Single-chamber ampoules preferably contain at least the two external walls that form the annulus into which the driven bush can be displaced.

BRIEF DESCRIPTION OF THE DRAWINGS

A preferred embodiment of the invention is described below with reference to the figures in which.

Description of the Preferred Embodiments

Figure 1:
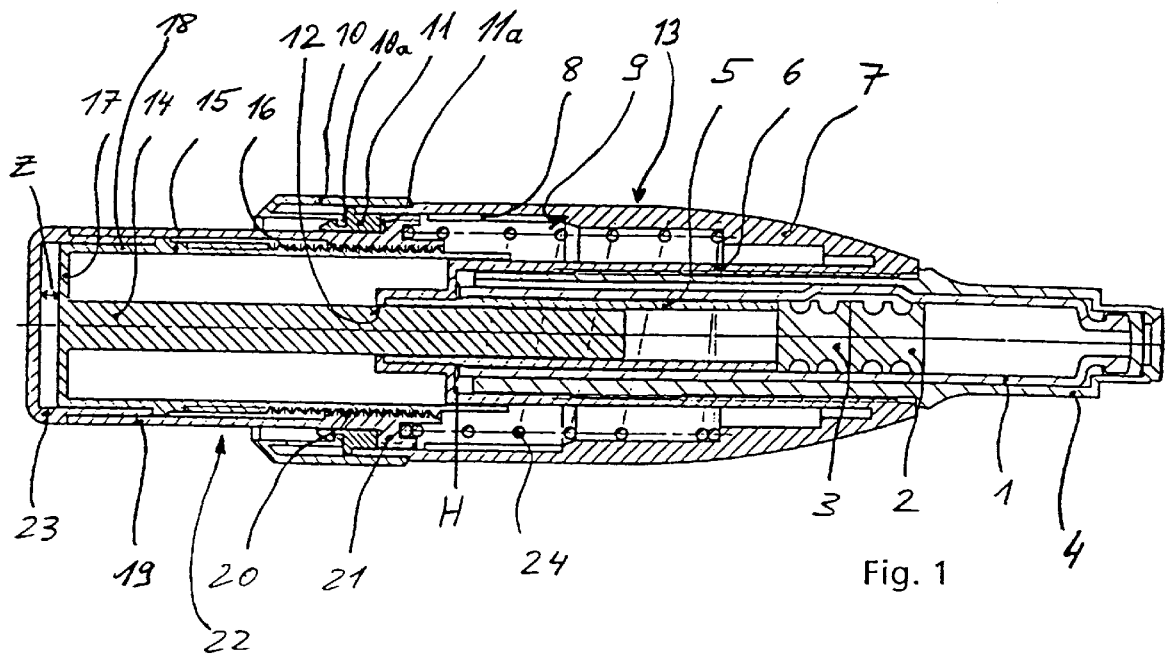
FIG. 1 shows a device according to the invention after the mixing of a drug solution.
Figure 2:
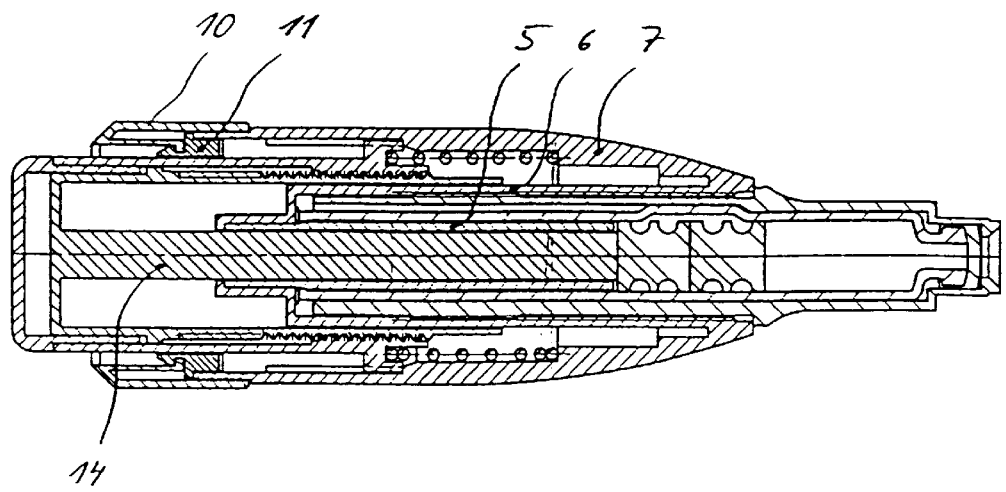
FIG. 2 shows the device of FIG. 1 after the removal of the residual air from the ampoule and FIG. 3 shows the device of FIGS. 1 and 2 after all the product has been released.
Figure 3:
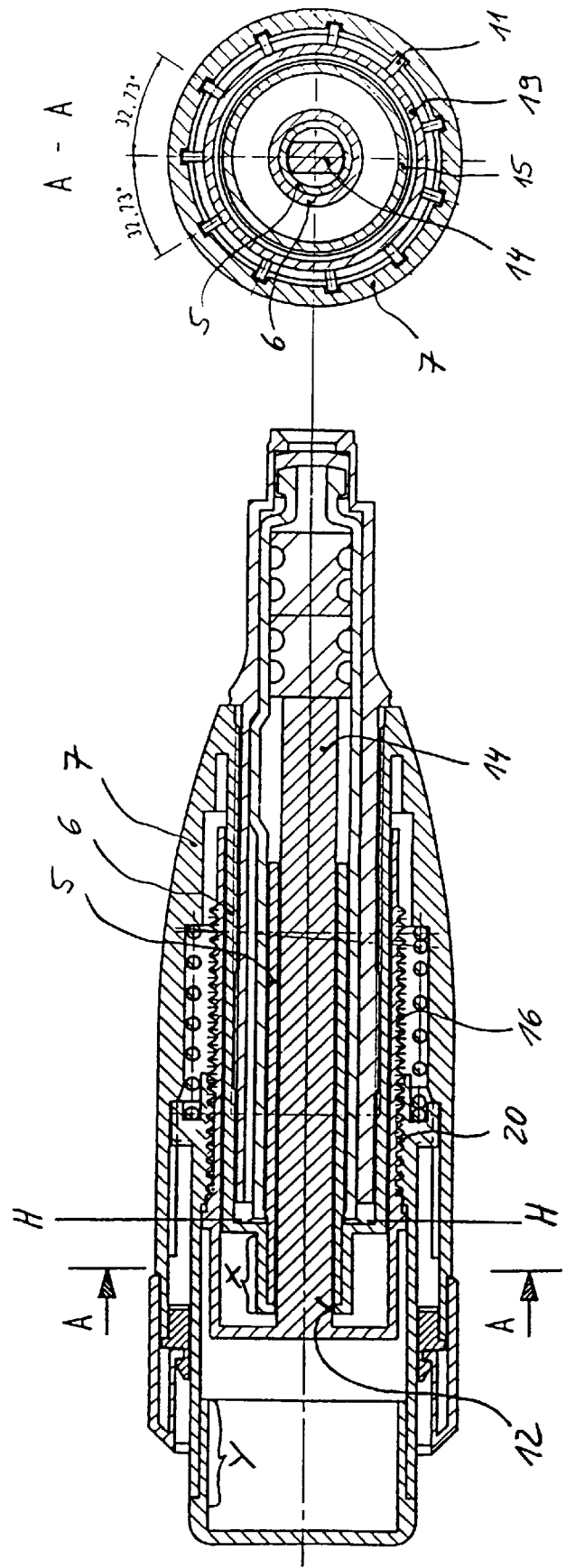

FIGS. 1 to 3 show the longitudinal section of an injection device in the form of a so-called pen with an inserted double-chamber ampoule 1.

FIG. 1 shows the injection pen directly after the insertion of the ampoule 1 into a housing 13. For insertion, the ampoule 1 is first slid into an ampoule bush 4. The ampoule bush 4 is open at the back to allow the insertion of the ampoule 1 and contains suitable stop surfaces with which the ampoule 1 is in full contact when inserted. The ampoule bush 4 containing the ampoule 1 is then inserted into housing 13 and fixed; it is at least secured against displacement and preferably also against rotation. In the embodiment of the invention it is screwed into the housing 13 until it makes contact with a stop face on the housing side once it has been inserted up to the end position in the housing 13.

The double-chamber ampoule 1 is circular cylindrical and is around its center widened on one side. The outlet at the front end of the ampoule, or the right end of the ampoule 1 in the Figure, is still sealed by a membrane. This membrane is pierced by an injection needle prior to the use of the ampoule 1. Ampoule 1 displaceably accommodates two pistons 2 and 3 arranged in series. In the initial state of the ampoule 1, a drug in powder form is contained in a front ampoule chamber, or in the Figure the right ampoule chamber, and a solution fluid is contained in a rear ampoule chamber formed between the two pistons 2 and 3. The injectable product, the drug solution, is formed by the rear piston 3 being slid forward against piston 2. This action forces the solution fluid through the widened side of the ampoule wall into the front chamber. The drug is then dissolved in the solution fluid after possibly a brief shaking of the ampoule or injection pen.

The housing 13 is mainly formed by three hollow cylindrical walls 5, 6 and 7. Between the internal first wall 5 and the middle second wall 6 and between the second wall 6 and the external third wall 7, an internal annulus open to the front and an external annulus open to the back remain. In the embodiment of the invention, the three hollow cylindrical walls 5, 6 and 7 are coaxially arranged to one another and their common longitudinal center axis coincides with the displacement axis along which the pistons 2 and 3 can be displaced. The three walls 5, 6 and 7 have a circular cylindrical cross section.

The first wall 5 protrudes from the rear into the inserted ampoule 1. The ampoule bush 4 is screwed to the second wall 6 that surrounds it once it has been inserted. The annulus formed between the first wall 5 and the second wall 6 thus serves as a retaining area for the ampoule 1. Before inserting the ampoule bush 4 containing the ampoule 1, an injection needle is screwed onto the ampoule bush 4. When the ampoule bush 4 is inserted, the needle pierces the rubber membrane of the bush 4. The rear piston 3 is then displaced towards the front piston 2 by pressing against an active front area of the first wall 5. This forces the solution fluid from the decreasing rear ampoule chamber via the widened section of the ampoule into the front ampoule chamber containing the drug. After insertion, the first wall 5 projects into the ampoule 1 to such an extent that in the ideal case, all of the solution fluid has been displaced into the front ampoule chamber, completely filling the front chamber. Because of its function, the first wall 5 is also referred to as mixing tube.

In order to release the drug solution, the two pistons 2 and 3 are displaced by pressing a driven member 18 towards the ampoule outlet, i.e. in feed direction. In FIG. 1, the driven member 18 is shown in a rear first position in which the product dose to be released with the next injection can be preset by a user. FIG. 1 shows the situation before the so-called priming, i.e. before the first release of the drug from the ampoule 1.

A drive member 22 engages into the driven member 18. The driven member 18 and the drive member 22 form a single-stage spindle drive via a thread pairing 16/20.

The drive member 22 contains a bush-shaped basic body 19 and is therefore hereinafter referred to as drive bush. The front area of the drive bush 19 contains an internal surface with a thread 20 that cooperates with a respective counter thread 16 on an external surface of the driven member 18 for selecting or pre-adjusting the product dose to be released with the next injection.

In the rear position of the drive means 18, 22 shown in FIG. 1, the drive bush 19 is pivotable around the longitudinal center axis that coincides with the displacement axis of the two pistons 2 and 3. Due to the pressure of a pressure spring 24, arranged in the annulus between the second and third housing wall 6 and 7, the drive means 18, 22 is pretensioned in its rear first position. For this purpose the pressure spring 24 is pretensioned under pressure between a circumferential shoulder on the housing side which radially projects inwards from the third housing wall 7 and a front face of the drive bush 19 serving as a counter bearing. In the rear first position of the drive means, a rear face of the drive bush 19 lies against a front face 11a of a lock ring 11. In this way, the rear first position of the drive means is defined. The lock ring 11 contains engaging means on its face 11a, such as radial grooves, which when turning the drive bush 19 allows a locking into place, also referred to as clicking, in the given angle positions or distances. The lock ring 11 is connected to the rear end of the third housing wall 7 by means such as screwing. Furthermore a closing bush 10 is provided that is rigidly connected to the housing wall 7 or pivotable around the longitudinal center axis of the injection device. Its snap-in hook 10a engages into a ribbed groove base of the lock ring 11. The drive bush 19 projects through the lock ring 11 and the closing bush 10.

The rear end of the drive bush 19 is closed by an inserted closing cap 23. The closing cap 23 is screwed into the drive bush 19, fixed to it by means of a catch or is rigidly connected to it in another way.

In the rear first position, the product dose to be released with the next injection is selected by rotating the drive bush 19. The driven member 18 is guided in a straight line and protected against rotation within the housing 13 so that when the drive bush 19 is turned via the thread pairing 16, 20, the driven member 18 is advanced towards the pistons 2 and 3. During the selection of the dose, i.e. the dosing, the clearance between the piston 3 and the active front area of the driven member 18 is set. The length of travel when the drive means 18, 22 is pressed in is always the same, so that the product dose to be released is set by adjusting the clearance. The length of the displacement path of the driven member 18 relative to the drive member 22 is limited by a front face of the closing cap 23 representing a rear stop and a facing front stop face of the drive bush 19. An internal surface of the closing cap 23 provides further guidance for the driven member 18. In FIG. 3 the length of this guide is shown as "y".

The length of displacement of the drive means 18, 22 is defined by the aforementioned rear stop on the lock ring 11 and a front stop 9 on the housing side. The front stop 9 is formed by a circumferential shoulder, radially protruding inward from the third housing wall 7. Between these two stops 9 and 11, the drive means 18, 22 can be displaced to and fro from the rear first position shown in FIG. 1 and a front second position shown in FIGS. 2 and 3.

Directly after having left the rear first position, the drive bush 19 engages into a straight guide 8 formed on an internal surface of the third housing wall 7 and is thus guided in a straight line as soon as it has left its rear first position towards its front second position.

In its rear first position, the drive means 18, 22 can generally also only be turned in discreet steps between specified lock-in positions so that the rotation position of the drive bush 19 cannot be inadvertently changed during the advancing movement.

The driven member 18 contains a central rod 14, hereinafter referred to as driven rod, a bush 15 surrounding the driven rod 14, hereinafter referred to as driven bush and a web 17 rigidly connecting the driven rod 14 and the driven bush 15 preventing their rotation and displacement in relation to one another. The driven member 18 has the shape of a pot in which the web 17 forms a disc-like bottom from which the driven bush 15, and in the middle the driven rod 14, rise up. In the embodiment of the invention, the driven rod 14, the driven bush 15 and the bottom 17 form a single-component driven member 18. An annulus is formed between the driven rod 14 and the driven bush 15 which accommodates the rear part of the ampoule 1 when the drive means 18, 22 is in its front second position (FIGS. 2 and 3). The driven rod 14 protrudes a little from the driven bush 15.

In order to form an anti-rotation protection between the housing 13 and the driven member 18, the driven rod 14 is flattened on two opposing sides over its entire length (FIG. 3). The flattened surfaces glide between two respective countersurfaces 12 of the housing 13. In addition or instead of the guide 12, the mixing tube 5 could be formed in such a way that it would provide the straight guide function. The internal surface of the driven bush 15 is also slidingly guided on an external surface of the second housing wall 6. This further improves the guidance of the drive means 18, 22. In order to prevent any possibility of jamming during the advancement from the rear first into the front second position, some of the driven bushing 15 already projects over the second housing wall 6 in its rear first position in the slide guide region.

The thread pairing 16/20 of the drive means 18, 22 almost reaches up to height H of the rear peripheral edge of ampoule 1; the thread section could even in the position of FIG. 1 project over height H in the feed direction. By transferring the contact between the drive member 22 and the driven member 18 from the driven rod 14 to the outside and the driven rod 14 and the drive bush 15 sliding over the ampoule 1 during injecting, the length of the device according to the invention can be kept to a minimum. As shown in FIG. 3, the driven bush 15 in its front position projects over the rear peripheral edge of the ampoule 1 at least after its discharge to such an extent that its entire thread area is positioned in front of the rear ampoule edge.

In FIG. 2 the pen of FIG. 1 is shown in its front second position in which the drive bush 19 is positioned against the front stop 9. Both pistons 2 and 3 have been moved slightly forward in ampoule 1 and have moved slightly off the front face of the first housing wall 5 so that a small product quantity is released. This is generally carried out before the first dosed injection during the so-called priming. For priming, the drive bush 19 is turned into the next click position, causing the driven member 18 to be moved forward a little. If the drive means 18, 22 is moved back from the front second position of FIG. 2 into the rear first position, the pen is ready for dosing and a subsequent injection.

FIG. 3 shows the same pen again in its front second position, however, after complete discharge of the ampoule 1, i.e. after a maximum dose has been administered. The driven bush 15 now takes up the largest part of the length, ideally the entire length of the external annulus between the second housing wall 6 and the third housing wall 7.

In the injection pen of the embodiment of the invention, the length could still be somewhat shortened if the bottom 17 of the driven member 18 could in the state shown in FIG. 3 be displaced even further towards the rear face of the ampoule 1. In the embodiment of the invention a rear step-like extension of the housing wall 6 does, however, prevent further sliding over the ampoule 1. On the other hand, this hollow cylindrical offset wall section of the second wall 6 serves as a retainer and guidance for the first housing wall 5, the mixing tube. In the embodiment of the invention, the first housing wall 5 is mainly designed as a simple hollow cylindrical bush in order to simplify the production of the housing 13. The bush is inserted in the hollow cylindrical extension of the second housing wall 6 where it is suitably retained. At the same time this design of the housing 13 facilitates the provision of the straight guide 12 for the driven member 18. The housing walls 5 and 6 can in principal also finish flat at their rear end even without the guiding elongation with step-like cross section, which would allow a further reduction of the length, i.e. the length x in FIG. 3. On the other hand, the guiding elongation facilitates the assembly in case of a retrospective flush insertion of the mixing tube 5. The length could be further reduced or could instead of the reduction of length x be saved to a lesser extent in the rear area above the driven member 18 between its web 17 and the closing cap 23, by shortening the length "z" in FIG. 1.

I claim:
1. Device for the dosed release of an injectable product, comprising
   a) a housing,
   b) a retainer for a container containing the product, in which a piston is displaceably accommodated, whose displacement in a feed direction causes the release of a product dose,
   c) a driven member including a driven rod which protruding into the container when the container is accommodated in the housing pushes the piston in the feed direction to release the product,
   d) at least one drive member engaging with the driven member, the driven member being displaced in the feed direction by the activation of the drive member, wherein
   e) the driven member contains a driven bush surrounding the driven rod, which driven bush engages into the drive member and is displaced together with the driven rod, and
   f) a rear wall—in relation to the feed direction—of the container protrudes at least during a release into an annulus formed between the driven rod and the driven bush.

2. Device according to claim 1, wherein the driven rod and the driven bush are a single component.

3. Device according to claim 1, wherein the driven member is pot-shaped and contains a bottom from which the driven rod and the driven bush rise up.

4. Device according to claim 1, wherein an anti-rotation protection is formed between the driven member and the housing by a slideway between a housing surface and a circumferential surface of the driven rod.

5. Device according to claim 1, wherein the drive member and the driven member form a spindle drive containing a thread pairing on an external surface of the driven bush and an internal surface of the bush-shaped drive member and that the bush parts of the spindle drive slide over the container like a shell.

6. Device according to claim 5, wherein a front end of the thread pairing in a forward position of the drive member is, at least after the complete discharge of the container, positioned at the same level as the rear end of the container or preferably even further back when viewed in feed direction.

7. Device according to claim 1, wherein the housing contains
   a) at least one wall surrounding the container and
   b) at least one further wall surrounding said wall, in which
   c) the driven bush is displaceable into an annulus formed between the two walls and shell-like at least over a rear part of the container.

8. Device according to claim 1, wherein the housing contains
   a) at least a hollow cylindrical first wall that can be inserted into the container,
   b) at least a cylindrical second wall surrounding the first wall and
   c) at least a cylindrical third wall surrounding the second wall, in which
   d) the driven rod is displaceable within the first wall and the driven bush within an annulus formed between the second and the third walls and in which a rear part of the container is accommodated in an annulus between the first and second walls.

9. Device according to claim 1, wherein the device is an injection pen for injecting a drug solution.

* * * * *

UNITED STATES PATENT AND TRADEMARK OFFICE
CERTIFICATE OF CORRECTION

PATENT NO. : 6,053,893
DATED : April 25, 2000
INVENTOR(S) : Eugen Bucher

It is certified that error appears in the above-identified patent and that said Letters Patent is hereby corrected as shown below:

<u>Title page,</u>
Please add: -- Priority Application: German patent application 197 40 187.2 filed September 12, 1997 --

<u>Column 1,</u>
After the heading "Background of the Invention," please insert:
-- This application claims the priority of German patent application no. 197 40 187.2 filed September 12, 1997, which is incorporated herein by reference. --

Signed and Sealed this

Eleventh Day of September, 2001

*Attest:*

*Attesting Officer*

NICHOLAS P. GODICI
*Acting Director of the United States Patent and Trademark Office*